(12) United States Patent
Sterk et al.

(10) Patent No.: US 6,689,799 B1
(45) Date of Patent: Feb. 10, 2004

(54) 1,4-DIHYDROPYRIDINE-5-CARBOXYLIC ACID ESTER DERIVATIVES AND METHOD FOR THE PREPARATION THEREOF

(75) Inventors: Geert Jan Sterk, Utrecht (NL); Jan Fetze Van Der Werf, Almere-Buiten (NL)

(73) Assignee: Rephartox, Onstwedde (NL)

( * ) Notice: Subject to any disclaimer, the term of this patent is extended or adjusted under 35 U.S.C. 154(b) by 48 days.

(21) Appl. No.: 10/069,216
(22) PCT Filed: Aug. 23, 2000
(86) PCT No.: PCT/NL00/00582

§ 371 (c)(1),
(2), (4) Date: Jun. 6, 2002

(87) PCT Pub. No.: WO01/14370

PCT Pub. Date: Mar. 1, 2001

(30) Foreign Application Priority Data

Aug. 23, 1999 (NL) .............................................. 1012886

(51) Int. Cl.[7] ....................... A61K 31/44; C07D 405/00
(52) U.S. Cl. ..................................... 514/337; 546/283.1
(58) Field of Search ....................... 514/337; 546/283.1

(56) References Cited

U.S. PATENT DOCUMENTS

| 4,564,619 A | * | 1/1986 | Tanaka et al. | ............... 514/312 |
| 5,545,646 A | | 8/1996 | Straub et al. | |
| 5,721,248 A | * | 2/1998 | Straub et al. | ............... 514/314 |

FOREIGN PATENT DOCUMENTS

| EP | 0194750 A | | 9/1986 |
| EP | 0 194 750 | * | 9/1986 |
| GB | 2127402 A | | 4/1984 |
| WO | WO 92 18132 A | | 10/1992 |

* cited by examiner

*Primary Examiner*—D. Margaret Seaman
(74) *Attorney, Agent, or Firm*—Stephen A. Slusher (57) ABSTRACT

The present invention relates to ester derivatives of 1,4-dihydropyridine-5-carboxylic acid of formula (I) wherein $R_1$, $R_2$ and $R_3$ may be a coumarin group. These compounds possess an anti-viral activity. Most of the anti-viral compounds known in the art are nucleoside-derivatives. Various viruses become resistant against these. Because the compounds according to the invention are not nucleoside-derivatives, they form a suitable alternative. The invention also relates to a method of preparing the anti-viral substances according to the invention.

20 Claims, 4 Drawing Sheets

1,4-DIHYDROPYRIDINE-5-CARBOXYLIC ACID ESTER DERIVATIVES AND METHOD FOR THE PREPARATION THEREOF

Figure 1:
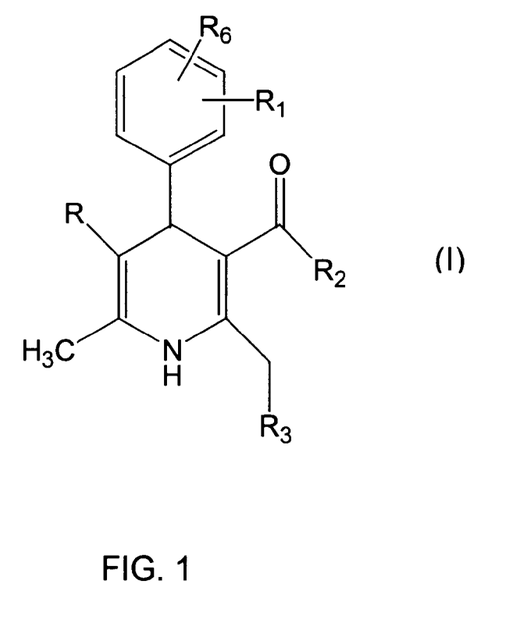
FIG. 1 depicts the compound of formula (I)
Figure 2:
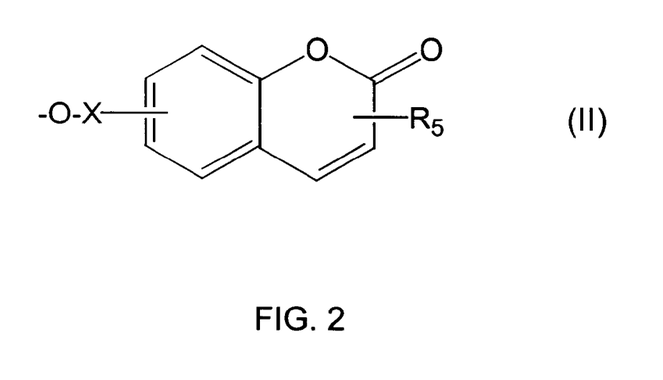
FIG. 2 depicts the compound of formula (II)

The present invention relates to ester derivatives of 1,4-dihydropyridine-5-carboxylic acid with the general formula I, (I)

wherein
R=CN, NO$_2$ or a —COOR' group, wherein R' represents a lower alkyl group;
R$_1$=R$_6$ or R$_4$;
R$_2$=lower alkoxy or R$_4$;
R$_3$=H or R$_4$;
R$_4$=a coumarin group with formula II;

(II)

R$_5$=H, lower alkyl, lower alkoxy, halogen, nitro, hydroxyl, or amino;
R$_6$=H, lower alkyl, lower alkoxy, benzyloxy, cyano, nitro, carboxylic acid, optionally esterified with a lower alkanol, carboxamide, optionally substituted with 1–2 lower alkyl groups;
X a single bond, —(CH2)$_n$—O—, of —(CH2)$_m$—Y—(CH2)$_k$—O, wherein n ranges from 1 to 6, m and k are each equal to or higher than 1 and the sum of m and k is smaller than or equal to 4; and
Y=phenylene, cycloalkylene, or a carbon atom substituted with 1 or 2 C$_{1-C2}$-alkyl groups;
with the provisio that lower alkyl, lower alkoxy, lower alkanol, benzyloxy, phenylene and cycloalkylene may optionally be substituted with 1–3 groups chosen from hydroxyl, cyano, amino, halogen, in particular chlorine or fluorine, and nitro;
under the condition that at least 1 of the groups R$_1$, R$_2$ and R$_3$ is the same as R$_4$, as well as the N-oxide, stereoisomers and/or addition salts thereof with a pharmaceutically acceptable acid or base;
where the term "lower alkyl" represents an optionally branched alkyl group having 1 to 6 carbon atoms, preferably 1 or 2 carbon atoms; the term "lower alkanol" represents a lower alkyl substituted with a hydroxyl group;
the term "lower alkoxy" represents an optionally branched alkoxy group having 1 to 6 carbon atoms, preferably 1 or 2 carbon atoms; and
the term "cycloalkyl" represents a cycloalkyl group having 3 to 8 carbon atoms.

It is remarked that more than 1 R$_1$, R$_5$, and R$_6$ groups may be present.
Halogen is to be understood as a halogen atom chosen from the group consisting of fluorine, chlorine, bromine or iodine, preferably fluorine or chlorine.

BACKGROUND OF THE INVENTION

1. Field of the Invention (Technical Field)

The present invention relates to 1,4-dihydropyridine-5-carboxylic acid ester derivatives, method for the preparation thereof, and methods for the treatment of disease using such derivatives.

2. Background Art

The largest group of antiviral compounds known in the art are nucleoside-analogues. One significant disadvantage of nucleoside-analogues is that virus strains progressively develop resistance against them. Thus there is a need in the art for compounds having antiviral activity that are not nucleoside-analogues.

Coumarin derivatives have been described in the literature as having antiviral activity. For example, International Patent Application WO 92/18123 describes coumarin derivatives and closely related compounds such as alkoxycoumarin derivatives. It is indicated that these compounds are suitable for inhibiting the replication of retroviruses.

SUMMARY OF THE INVENTION (DISCLOSURE OF THE INVENTION)

The present invention relates to three methods for preparing an ester derivative of 1,4-dihydropyridine-5-carboxylic acid.

The present invention is characterized in that either

Figure 3:
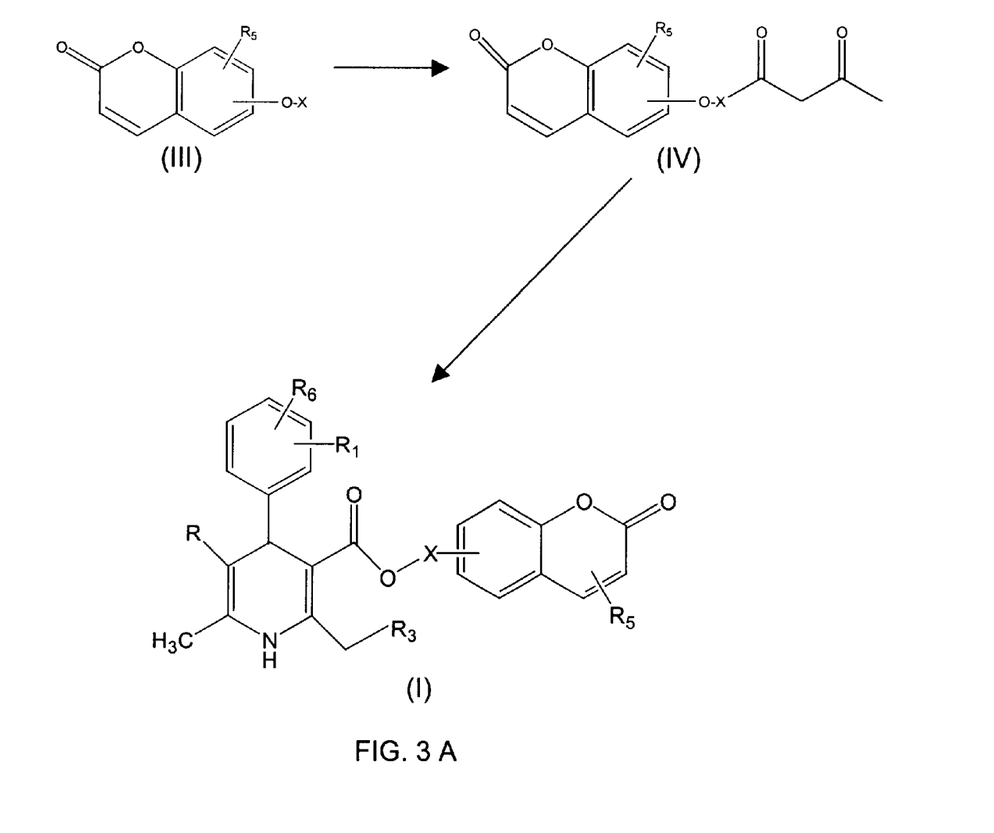
Figure 3B:
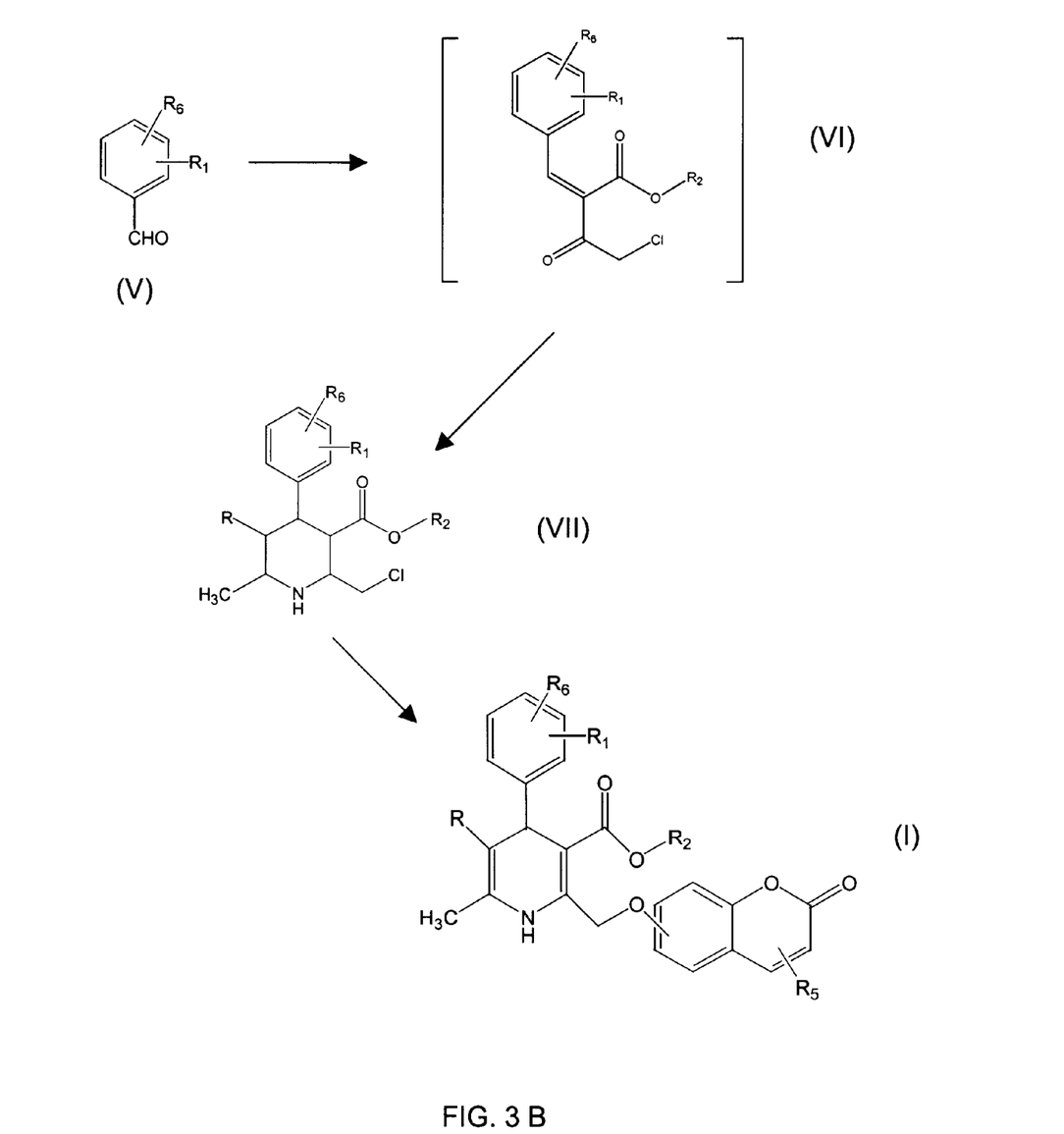
FIG. 3B depicts the reactions of method B for making the compound of formula (I); and, FIG. 3C depicts the reactions of method C for making the compound of formula (I).
Figure 3C:
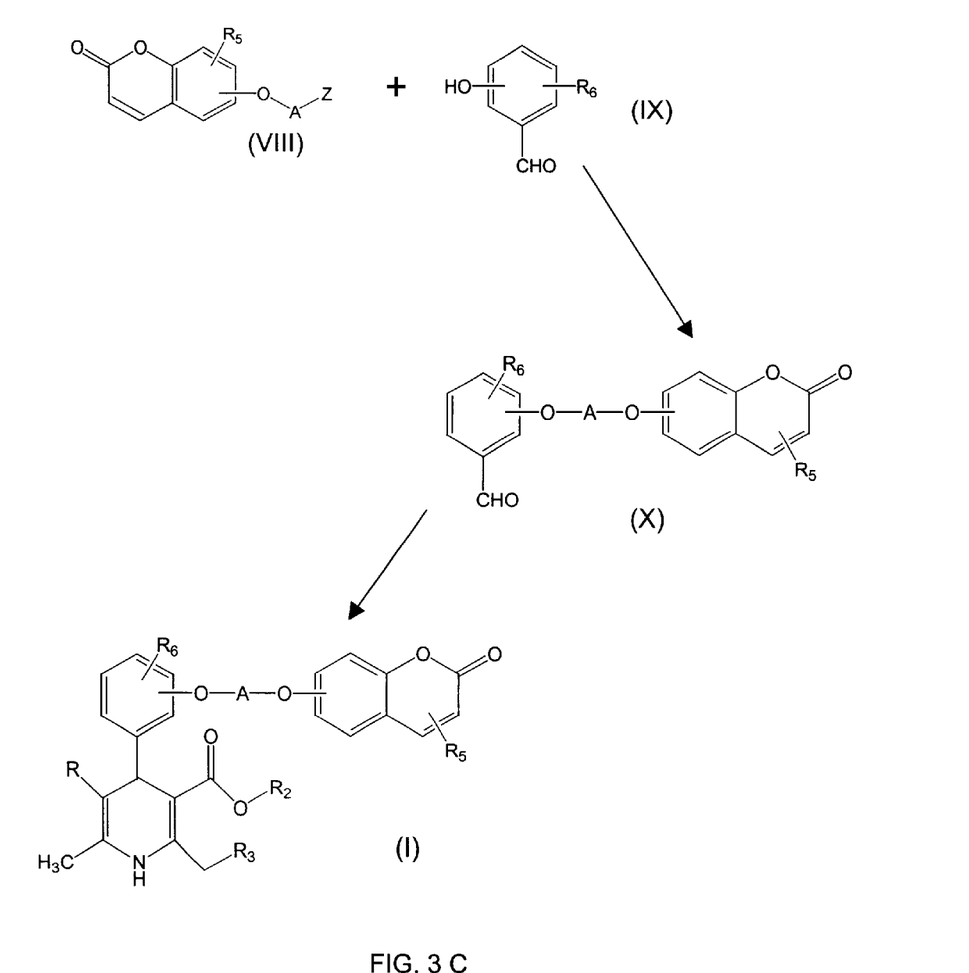

A. i) a coumarin derivative of the formula III (III)

is converted to an acetoacetate-ester having the general formula IV;

(IV)

ii) the acetoacetate-ester thus formed is reacted with a benzaldehyde having the formula V and an R'-aminocrotonate, wherein R' is as defined before, yielding the desired ester derivative of 1,4-dihydropyridine-5-carboxylic acid; or, B. i) a benzaldehyde derivative of the formula V,

(V)

wherein $R_1$ and $R_6$ are as defined before, is reacted with an $R_2$-4-chloroacetoacetate, wherein $R_2$ is as defined before, yielding a benzylidene of the formula VI;

(VI)

ii) the benzylidene formed in the previous step is reacted with an R'-3-aminocrotonate, wherein R' is as defined before, yielding a 5-chloromethyl-1,4-dihydropyridine derivative of the formula VII;

(VII)

iii) the 5-chloromethyl-1,4-dihydropyridine derivative formed in step ii) is reacted under basic conditions with a coumarin derivative of the formula III, where X and $R_5$ are as defined before, yielding the desired ester derivative of 1,4-dihydropyridine-5-carboxylic acid; or, C. i) a coumarin derivative of the formula VIII;

(VIII)

where Z represents a leaving group and $R_5$ is as defined before, while A represents $-(CH2)_n-$, or $-(CH2)_m-Y-(CH2)_k-$ where n, m and k are as defined for X, are reacted under basic conditions with a benzaldehyde derivative of the formula V, where $R_1$ and $R_6$ have the meaning as defined before, yielding a Williamson ether of the formula IX;

(IX)

ii) the Williamson ether is reacted with an R'-3-aminocrotonate derivative yielding the desired ester derivative of 1,4-dihydropyridine-5-carboxylic acid.

With respect to the method described under A, it is remarked that step A i) is conducted as described by Clemens R. J. et al. (J. Org. Chem. 50, pages 646–652, 1980). Step A. ii) concerns a Michael-addition reaction which is suitably performed in a polar solvent (such as methanol, ethanol or 2-propanol) and is described by Stout D. M. et al. (Chem. Rev. 82, pages 233–243, 1982).

With respect to the method described under B, it is remarked that the product (VI) obtained in step B i) does not have to be isolated, but can be condensated immediately in the subsequent step with the 3-aminocrotonate. The last step B. iii) concerns a preparation of a so-called Williamson ether ((Meerwein H., Methoden der Organischen Chemie (Houben Weyl) 6/3, p. 6–140).

Finally, with respect to the method described under C, it is remarked that step C i) concerns the preparation of a Williamson ether, which is performed under influence of a suitable base (such as potassium- or sodiumcarbonate, sodiumhydride, or triethylamine) in a polar inert solvent (for example methanol, acetone, dimethylformamide or dioxane). The second step C. ii) is again a Michael-addition, as described under step A. ii).

The present invention further relates to a pharmaceutical composition comprising a compound according to the invention together with a pharmaceutically acceptable carrier or excipient.

Finally, the present invention relates to a pharmaceutical composition containing an ester derivative of 1,4-dihydropyridine-5-carboxylic acid according to the invention as the active compound, suitable for the treatment of a viral affliction, high blood pressure or glaucoma.

The viral afflictions may be such viral afflictions caused by:
1 Adenovirus type 2
2 Coxsackie virus B4
3 Cytomegalovirus (AD-169 strain; Davis strain)
4 Herpes simplex virus 1 (KOS; F; McIntyre; TK-B2006; TK-VMW1837; TK-Cheng C158/77; TK-Field C137/101)
5 Herpes simplex virus-2 (G; 196; Lyons)
6 HIV-1
7 HIV-2
8 Influenza virus A
9 Influenza virus B
10 Parainfluenza-3 virus
11 Polio virus-1
12 Reovirus
13 Respiratory syncytial virus
14 Semliki forest virus
15 Sindbis virus
16 Vaccinia virus
17 Varicella zoster virus (TK$^+$ OKA strain; TK$^+$ YS strain; TK$^-$ 07/1 strain; TK$^-$ YS/R strain;
18 Vesicular stomatitus virus.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 3A depicts the reactions of method A for making the compound of formula (I);

DESCRIPTION OF THE PREFERRED EMBODIMENTS (BEST MODES FOR CARRYING OUT THE INVENTION)

The present invention will now be elucidated with reference to the following exemplifying embodiments and in vivo experiments. Starting materials are either commercially available, or are analogous to known compounds easily prepared by the ordinary person skilled in the art. Known starting materials are described in PCT WO 94/12488.

The formula sheet referred to in this specification is formed by the drawing which, apart from the formulas I and II, schematically shows three methods.

General Description of the Preparation According to Method A

First Step: Preparation of a Coumarinyloxyalkylacetoacetate.

A mixture of 50 mmoles of a hydroxyalkoxycoumarin, 50 mmoles 2,2,6-trimethyl-(1,3)-dioxin-4-on and 5 mmoles 4-toluenesulphonic acid is heated for 5 hours at a temperature of 110–120° C. Subsequently the crude end product thus obtained is purified using column chromatography over silica (Baker 7024-02). Elution is usually performed with 1:1 ethylacetate:pet. ether (60–80). In addition or alternatively, purification was done by means of crystallization from the solvent indicated. The usual yield is about 60%.

Second Step: Formation of a Coumarinyloxyalkoxycarbonyldihydropyridine.

A solution of 10 mmoles of the coumarinyloxyalkylacetoacetate, obtained in the first step, 10 mmoles of a benzaldehyde and 1 mmole of benzylammoniumacetate in 50 ml 2-propanol is heated under reflux for 18 hours. After addition of 10 mmoles of an alkyl-3-aminocrotonate, heating under reflux is continued for another 24 hours. After evaporation of the solvent, the residue is dissolved in ethylacetate and washed with a 1 N potassiumhydroxide solution. The ethylacetate solution is dried over magnesiumsulphate, filtrated and evaporated. Working up is as described in the first step. The yield is usually about 35%.

General Description of the Preparation According to Method B

First Step: Preparation of 2-Chloromethyl-1,4-dihydropyridine.

A mixture of 0,1 mol of a benzaldehyde, 0,1 mol ethyl-4-chloroacetoacetate and 5 mmoles of benzylammoniumacetate in 100 ml 2-propanol is stirred for 3 days at room temperature, after which the solvent is evaporated. The residue is dissolved in 250 ml methanol and 0,1 mol of an alkyl-3-aminocrotonate is added. The resulting solution is stirred for 7 days at room temperature. After addition of 5 ml concentrated hydrochloric acid stirring is continued for another 24 hours at room temperature, after which the mixture is filtrated. The solution is reduced to about 20% of the original volume using a rotatory evaporator, whereafter the intermediate product crystallizes. Usual yield: ca. 40%.

Second Step: Preparation of 2-Coumarinyloxymethyl-1,4-dihydropyridine.

A mixture of 10 mmoles of a hydroxycoumarine, 10 mmoles of the intermediate product obtained in the previous step and 10 mmoles potassiumcarbonate are heated for 90 minutes in 25 ml anhydrous dimethylformamide at 70–80° C. After cooling, 200 ml water is added and the solution is extracted with 200 ml of ethylacetate. The organic layer is separated, dried over magnesiumsulphate, filtrated and evaporated. The product is purified using column chromatography and/or crystallization, as described for method A. Usual yield: ca. 25%.

General Description of the Preparation According to Method C

First Step: Preparation of a (Formylphenoxy) alkoxycoumarin.

A mixture of 50 mmoles of a bromoalkoxycoumarin, 50 mmoles of a hydroxybenzaldehyde and 70 mmoles anhydrous potassiumcarbonate in 100 ml anhydrous dimethylformamide is heated for 2 hours at 90–110° C. under a flow of anhydrous nitrogen. After cooling to room temperature, 300 ml water is added and the mixture extracted with 300 ml ethylacetate. The organic layer is separated, dried over magnesiumsulphate, filtrated and evaporated using a rotatory evaporator. The residue is purified using column chromatography (eluent: 1:1 ethylacetate:pet. ether (60–80)). Crystallization from diethylether. Usual yield: ca. 70%.

Second Step: Preparation of a 4-(Coumarinyloxyalkoxyphenyl)dihydropyridine.

A solution of 10 mmoles of a (formylphenoxy) alkoxycoumarin (first step), 25 mmoles of an alkyl-3-aminocrotonate and 1 mmole of benzylammoniumacetate in 100 ml 2-propanol is heated under reflux for 18 hours. After evaporation of the solvent, the residue is purified by means of crystallization, yielding the product with a usual yield of ca. 40%.

The compounds according to the Examples 1–18 were prepared according to method A.

EXAMPLE 1

2,6-Dimethyl-4-phenyl-5-methoxycarbonyl-3-[{2-(coumarin-4-yloxy)ethoxy}carbonyl]-1,4-dihydropyridine Preparation of the Intermediate 2-(Coumarin-4-yloxy)-ethyl-acetoacetate Starting material: 4-(2-hydroxyethoxy)coumarin. Crystallized from ethylacetate. Fp.: 111–115° C.

Preparation of the title product:

Starting materials: benzaldehyde and methyl-3-aminocrotonate.

Crystallized from methanol. Fp.: 186–192° C.

$^1$H-NMR (CDCl$_3$): 2.33 (s; 3H; CH$_3$); 2.40 (s; 3H; CH$_3$); 3.60 (s; 3H; OCH$_3$); 4.13–4.70 (m; 4H; CH$_2$—CH$_2$); 4.98 (s; 1H; Ar—H); 5.61 (s; 1H; Ar—H); 5.86 (bs; 1H; NH); 7.00–7.80 (m; 9H; Ar—H).

EXAMPLE 2

2,6-Dimethyl-4-(2-nitrophenyl)-5-methoxycarbonyl-3-[{2-(4-methylcoumarin-7-yloxy) ethoxy}carbonyl]-1,4-dihydropyridine Preparation of the Intermediate 2-(4-Methylcoumarin-7-yloxy)ethylacetoacetate Starting material: 7-(2-hydroxyethoxy)-4-methylcoumarin. Crystallized from ethylacetate. Fp.: 90–95° C.

$^1$H-NMR (CDCl$_3$): 1.98 (s; 0.3H; CH$_3$—CO enol form); 2.30 (s; 2.7H; CH$_3$—CO keto form); 2.45 (s; 3H; CH$_3$-coum); 3.54 (s; 2H; CO—CH$_2$—CO); 4.21–4.32 (m; 2H; coum-O—CH$_2$); 4.48–4.62 (m; 2H; CO—O—CH$_2$); 5.09 (s; 0.1H; CH=C—); 6.18 (s; 1H; Ar—H); 6.79–6.95 (m; 2H; Ar—H); 7.45–7.58 (m; 1H; Ar—H).

Preparation of the title product

Starting materials: 2-nitrobenzaldehyde and methyl-3-aminocrotonate. Crystallized from methanol. Fp.: 198–201° C.

EXAMPLE 3

2,6-Dimethyl-5-methoxycarbonyl-3-[{2-(4-methylcoumarin-7-yloxy)ethoxy}carbonyl]-4-(3-nitrophenyl)-1,4-dihydropyridine $^1$H-NMR (CDCl$_3$): 2.38–2.47 (m; 9H; 2.6-diCH$_3$, CH$_3$-coum); 3.67 (s; 3H; CH$_3$—O); 4.09–4.24 (m; 2H; coum-O—CH$_2$); 4.29–4.60 (m; 2H; CO—O—CH$_2$); 5.10 (s; 1H; DHP-H$_4$); 5.93 (s; 1H; NH); 6,18 (s; 1H; Ar—H); 6.70–6.86 (m; 2H; Ar—H); 7.20–8.10 (m; 5H; Ar—H).

The first step is identical to that of Example 2.

Preparation of the title product:

Starting materials: 3-nitrobenzaldehyde and methyl-3-aminocrotonate. Purified using column chromatography (eluent: ethylacetate). Crystallized from methanol. Fp.: 213–217° C.

EXAMPLE 4

3-[{3-(Coumarin-4-yloxy)-1-propoxy}carbonyl]-2,6-dimethyl-5-methoxycarbonyl-4-phenyl-1,4-dihydropyridine Preparation of the Intermediate 3-(Coumarin-4-yloxy)-1-propylacetoacetate Starting material: 4-(3-hydroxy-1-propoxy)coumarin. Purified using column chromatography (eluent: 1:1 ethylacetate:pet. ether (60–80)). Crystallized from ethylacetate. Fp.: 71–75° C.

Preparation of the title product:

Starting materials: benzaldehyde and methyl-3-aminocrotonate. Purified using column chromatography (eluent: 1:1 ethylacetate:pet. ether (60–80)). Crystallized from ethylacetate. Fp.: 205–207° C.

EXAMPLE 5

3-[{3-(Coumarin-4-yloxy)propoxylcarbonyl]-2,6-dimethyl-5-methoxycarbonyl-4-(2-trifluoromethylphenyl)-1,4-dihydropyridine The first step is identical to that of Example 4.

Preparation of the title product:

Starting materials: 2-trifluoromethylbenzaldehyde and methyl-3-aminocrotonate. Purified using column chromatography (eluent: 1:1 ethylacetate:pet. (60–80)). Crystallized from methanol. Fp.: 174–1770C.

EXAMPLE 6

3-[{3-(Coumarin-4-yloxy)-2,2-dimethyl-1-propoxy}carbonyl]-2,6-dimethyl-5-methoxycarbonyl-4-phenyl-1,4-dihydropyridine Preparation of the Intermediate 3-(Coumarin-4-yloxy)-2,2-dimethyl-1-propylacetoacetate Starting material: 4-(3-hydroxy-2,2-dimethyl-1-propyloxy)coumarin. Crystallized from diethylether. Fp.: 107–110° C.

Preparation of the title product:

Starting materials: benzaldehyde and methyl-3-aminocrotonate. Purified using column chromatography (eluent: 1:1 ethylacetate:pet. ether (60–80)). Crystallized from diethylether. Fp.: 152–156° C.

EXAMPLE 7

2,6-Dimethyl-4-phenyl-5-methoxycarbonyl-3-[{2 (coumarin-4-yloxy)ethoxy}carbonyl]-1,4-dihydropyridine Preparation of the Intermediate 2-2-[2-(Coumarin4-yloxy)ethoxy]ethoxy}ethylacetoacetate Starting material: 4-{2-[2-(2-Hydroxyethoxy)ethoxy]ethoxy}coumarin. Purified using column chromatography (eluent: 1:1 ethylacetate:pet. ether (60–80)). Crystallized from diethylether. Fp.: 70–74° C.

Preparation of the title compound:

Starting materials: benzaldehyde and methyl-3-aminocrotonate. Purified using column chromatography (eluent: 1:1 ethylacetate:pet. ether (60–80)). Crystallized from diethylether. Fp.: 46–49° C.

EXAMPLE 8

3-[{3-(Coumarin-4-yloxy)-1-propoxy}carbonyl]-2,6-dimethyl-5-ethoxycarbonyl-4-(2-trifluoromethylphenyl)-1,4-dihydropyridine The preparation of the intermediate is described in Example 4.

Preparation of the title product:

Starting materials: 2-trifluoromethylbenzaldehyde and ethyl-3-aminocrotonate. Purified using column chromatography (eluent: 1:1 ethylacetate:pet. ether (60–80)). Crystallized from ethanol. Fp.: 153–155° C.

EXAMPLE 9

2,6-Dimethyl-5-methoxycarbonyl-3-[{2-(4-methylcoumarin-7-yloxy)ethoxy}carbonyl]-4-(2-trifluoromethylphenyl)-1,4-dihydropyridine The preparation of the intermediate is described in Example 2.

Preparation of the title product:

Starting materials: 2-trifluoromethylbenzaldehyde and ethyl-3-aminocrotonate. Purified using column chromatography (eluent: 1:1 ethylacetate:pet. ether (60–80)). Crystallized from methanol. Fp.: 194–197° C.

EXAMPLE 10

2,6-Dimethyl-5-methoxycarbonyl-3-[{2-(4-methylcoumarin-7-yloxy)ethoxy}carbonyl]-4-(2-trifluoromethylphenyl)-1,4-dihydropyridine The preparation of the intermediate is described in Example 2.

Preparation of the title compound:

Starting materials: 2-trifluoromethylbenzaldehyde and methyl-3-aminocrotonate. Purified using column chromatography (eluent: 1:1 ethylacetate:pet. ether (60–80)). Crystallized from methanol. Fp.: 80–82° C.

EXAMPLE 11

3-[{3-(Coumarin-4-yloxy)-2,2-dimethyl-1-propoxy}carbonyl]-2,6-dimethyl-5-ethoxy-carbonyl-4-(2trifluoromethyl)phenyl-1,4-dihydropyridine The preparation of the intermediate is described in Example 6.

Preparation of the title product:

Starting materials: 2-trifluoromethylbenzaldehyde and ethyl-3-aminocrotonate. Purified using column chromatography (eluent: 1:1 ethylacetate:pet. ether (60–80)). Crystallized from ethylacetate/pet. ether (60–80). Fp.: 186–190° C.

EXAMPLE 12

3-[{3-(4-Methylcoumarin-7-yloxy)-1-propoxy}carbonyl]-2,6-dimethyl-5-ethoxycarbonyl-4-(2-trifluoromethylphenyl)-1,4-dihydropyridine Preparation of the Intermediate 3-(4-Methylcoumarin-7-yloxy)-1-propylacetoacetate Starting material: 7-(3-hydroxy-1-propoxy)-4-methylcoumarin. Purified using column chromatography (eluent: 1:1 ethylacetate:pet. ether (60–80)). Fp.: 61–66° C.

Preparation of the title compound:

Starting materials: 2-trifluoromethylbenzaldehyde and ethyl-3-aminocrotonate. Purified using column chromatography (eluent: 1:1 ethylacetate:pet. ether (60–80)). Crystallized from ethylacetate/pet. ether 60–80. Fp.: 74–76° C.

EXAMPLE 13

3-[{4-(Coumarin-4-yloxy)methyl[trans]cyclohexyl}methoxycarbonyl]-2,6-dimethyl-5-ethoxycarbonyl-4-(2-trifluoromethylphenyl)-1,4-dihydropyridine Preparation of the Intermediate 4-[(Coumarin-4-yloxy)methyl][trans]cyclohexylmethylacetoacetate.

Starting material: 4-[(4-hydroxymethyl[trans]cyclohexyl)methoxy]coumarin. Purified using column chromatography (eluent: 1:1 ethylacetate:pet. ether (60–80)). Fp.: 72–76° C.

Preparation of the title compound:

Starting materials: 2-trifluoromethylbenzaldehyde and ethyl-3-aminocrotonate. Purified using column chromatography (eluent: 1:1 ethylacetate:pet. ether (60–80)). Crystallized from methanol. Fp.: 83–85° C.

EXAMPLE 14

3-[{3-(Coumarin-4-yloxy)-1-propoxy}carbonyl]-2,6-dimethyl-5-isopropoxycarbonyl-4-(2-trifluoromethylphenyl)-1,4-dihydropyridine The preparation of the intermediate is described in Example 4.

Preparation of the title product:

Starting materials: 2-trifluoromethylbenzaldehyde and isopropyl-3-aminocrotonate. Purified using column chromatography (eluent: 1:1 ethylacetate:pet. ether (60–80)). Crystallized from ethanol. Fp.: 155–156° C.

EXAMPLE 15

2,6-Dimethyl-5-isopropyloxycarbonyl-4-(2-trifluoromethylphenyl)-3-[{2-(3,4,8-trimethylcoumarin-7-yloxy)ethoxy}carbonyl]-1,4-dihydropyridine Preparation of the Intermediate 2-(3,4,8-Trimethylcoumarin-7-yloxy)ethylacetoacetate Starting material: 7-(2-hydroxyethoxy)-3,4,8-trimethylcoumarin. Crystallized from ethylacetate. Fp.: 114–116° C.

Preparation of the title compound:

Starting materials: 2-trifluoromethylbenzaldehyde and isopropyl-3-aminocrotonate. Purified using column chromatography (eluent: 1:1 ethylacetate:pet. ether (60–80)). Crystallized from ethanol. Fp.: 78–81° C.

EXAMPLE 16

2,6-Dimethyl-5-methoxycarbonyl-4-(2-trifluoromethylphenyl)-3-[{2-(3,4,8-trimethylcoumarin-7yloxy)ethoxy)}carbonyl]-1,4-dihydropyridine The preparation of the intermediate is described in Example 15.

Preparation of the title compound:

Starting materials: 2-trifluoromethylbenzaldehyde and methyl-3-aminocrotonate. Purified using column chromatography (eluent: 1:1 ethylacetate:pet. ether (60–80)). Crystallized from ethanol. Fp.: 79–82° C.

EXAMPLE 17

4-(2-Benzyloxyphenyl)-2,6-dimethyl-5-isopropylxycarbonyl-3-[2-((3,4,8-trimethyl-coumarin-7-yl)oxyethoxycarbonyl]-1,4-dihydropyridine The preparation of the intermediate is described in Example 15.

Preparation of the title product:

Starting materials: 2-benzyloxybenzaldehyde and isopropyl-3-aminocrotonate. Purified using column chromatography (eluent: 1:1 ethylacetate:pet. ether (60–80)). Crystallized from ethanol. Fp.: 187–191° C.

EXAMPLE 18

4-(2-Benzyloxyphenyl)-2,6-dimethyl-5-ethoxycarbonyl-3-[2-{(3,4,8-trimethylcoumarin-7-yl)oxyethoxy}carbonyl]-1,4-dihydropyridine The preparation of the intermediate is described in Example 15.

Starting materials: 2-benzyloxybenzaldehyde and ethyl-3-aminocrotonate. Purified using column chromatography (eluent: 1:1 ethylacetate:pet. ether (60–80)). Crystallized from ethanol. Fp.: 103–106° C.

Compounds according to the Examples 19–27 were prepared according to method B.

EXAMPLE 19

2-(4-Methylcoumarin-7-yloxymethyl)-3,5-diethoxycarbonyl-6-methyl-4-(3-nitrophenyl)-1,4-dihydropyridine Preparation of the Intermediate 2-Chloromethyl-3,5-diethoxycarbonyl-6-methyl-4-(3-nitrophenyl)-1,4-dihydropyridine.

Starting materials: 3-nitrobenzaldehyde, ethyl-4-chloroacetoacetate and ethyl-3-aminocrotonate. Fp.: 116–118° C.

Preparation of the title compound:

Starting material: 7-hydroxy-4-methylcoumarin. Fp.: 235–238° C.

$^1$H-NMR (CDCl$_3$): 1.15–1.35 (m; 6H; 2×ester CH$_3$); 2.53 (s; 3H; CH$_3$); 4.03–4.21 (m; 4H; 2×ester CH$_2$); 5.14 (s; 1H; Ar—H); 5.38 (s; 2H; coum-CH$_2$); 6.20 (s; 1H; NH); 6.87–7.03 (m; 3H; Ar—H); 7.50 (t; J=7.0 Hz; 1H; Ar—H); 7.51–7.70 (m; 2H; Ar—H); 8.00–8.17 (in; 2H; Ar—H).

EXAMPLE 20

2-(Coumarin-4-yloxymethyl)-3,5-diethoxycarbonyl-6-methyl-4-(3-nitrophenyl)-1,4-dihydropyridine The preparation of the intermediate is described in Example 19.

Preparation of the title product:
Starting material: 4-hydroxycoumarin. Fp.: 76–79° C.

EXAMPLE 21

2-(3-Methylcoumarin-4-yloxymethyl)-3,5-diethoxycarbonyl-6-methyl-4-(3-nitrophenyl)-1,4-diydropyridine The preparation of the intermediate is described in Example 19.

The preparation of the title product:
Starting material: 4-hydroxy-3-methylcoumarin. Fp.: 161–164° C.

EXAMPLE 22

2-(4-Methylcoumarin-7-yloxymethyl)-3,5-diethoxycarbonyl-6-methyl-4-(2-nitrophenyl)-1,4-dihydropyridine The Preparation of the Intermediate 2-Chloromethyl-3,5-diethoxycarbonyl-6-methyl-4-(2-nitrophenyl)-1,4-dihydropyridine.

Starting materials: 2-nitrobenzaldehyde, ethyl-4-chloroacetoacetate and ethyl-3-aminocrotonate. Fp.: 93–95° C.

Preparation of the title compound:
Starting material: 7-hydroxy-4-methylcoumarin. Fp.: 167–171° C.

EXAMPLE 23

2-(3-Ethylcoumarin-4-yloxymethyl)-3,5-diethoxycarbonyl-6-methyl-4-(3-nitrophenyl)-1,4-dihydropyridine The preparation of the intermediate is described in Example 19.

Preparation of the title compound:
Starting material: 3-ethyl-4-hydroxycoumarin. Fp.: 172–173° C.

EXAMPLE 24

2-(Coumarin-4-yloxymethyl)-3,5-diethoxycarbonyl-6-methyl-4-(2-trifluoromethylphenyl)-1,4-dihydropyridine The Preparation of the Intermediate 2-Chloromethyl-3,5-diethoxycarbonyl-6-methyl-4-(2-trifluoromethylphenyl)-1,4-dihydropyridine Starting materials: 2-trifluoromethybenzaldehyde, ethyl-4-chloroacetoacetate and ethyl-3-aminocrotonate. Fb: 160–161° C.

Preparation of the title compound:
Starting material: 4-hydroxycoumarin. Fp.: 179–181° C.

EXAMPLE 25

2-Chloromethyl-3,5-diethoxycarbonyl-6-methyl-4-(2-trifluoromethylphenyl)-1,4-dihydropyridine The preparation of the intermediate is described in Example 24.

Preparation of the title product:
Starting material: 3-(α-acetonylbenzyl)-4-hydroxycoumarin. Fp.: 201–202° C.

EXAMPLE 26

2-(3-Chloro-4-methylcoumarin-7-yloxymethyl-di-ethoxycarbonyl-6-methyl-4-(3-nitrophenyl)1,4-dihydropyridine The preparation of the intermediate is described in Example 19.

Preparation of the title compound:
Starting material: 3-chloro-7-hydroxy-4-methylcoumarin. Fp.: 255–260° C.

EXAMPLE 27

2-(3-Bromo-4-methylcoumarin-7-yloxymethyl)3,5-diethoxycarbonyl-6-methyl-4-(3-nitrophenyl)-1,4-dihydropyridine The preparation of the intermediate is described in Example 19.

Starting material: 3-bromo-7-hydroxy-4-methylcoumarin. Fp.: 221–224° C.

The compounds according to the Examples below were prepared according to method C.

EXAMPLE 28

4-[{4-(4-Methyl-7-coumarinyloxy)-1-butoxy}phenyl]-3,5-dimethoxycarbonyl-2,6-dimethyl-1,4-dihydropyridine Preparation of the Intermediate 7-{4-(2-Formylphenoxy)-1-butoxy}-4-methylcoumarin.

Starting materials: 7-(4-bromo-1-butoxy)-4-methylcoumarin and salicylaldehyde. Fp.: 110–111° C.

$^1$H-NMR (CDCl$_3$): 1.96–2.19 (m, 4H, C—CH$_2$—CH$_2$—C); 2.32–2.46 (m, 3H, coum. —CH$_3$); 4.01–4.32 (m, 4H, 2×OCH$_2$); 6.08–6.19 (m, 1H, coum. —H$_3$); 6.75–7.16 (m, 4H, Ar—H); 7.39–7.92 (m, 3H, Ar—H); 10.55 (s, 1H, CHO).

Preparation of the title product:
Starting material: methyl-3-aminocrotonate. Crystallized from ethanol. Fp.: 202–205° C.

$^1$H-NMR (CDCl$_3$): 1.88–2.48 (m; 13H; C—CH$_2$—CH$_2$—C; 2,6-diCH$_3$; coum-CH$_3$); 3.59 (s; 6H; 2×OCH$_3$); 3.93–4.30 (m; 4H; 2×OCH$_2$); 5,29 (s; 1H; DHP-H$_4$); 5.87 (bs; 1H; NH); 6.13–6.23 (m; 1H; coum H$_3$); 6.71–7.64 (m; 7H; Ar—H).

EXAMPLE 29

4-[{4-(-Coumarinyloxy)-1-butoxy}phenyl]3,5-dimethoxycarbonyl-2,6-dimethyl-1,4-dihydropyridine Preparation of the Intermediate 4-{4-(2-Formylphenoxy)-1-butoxy}coumarin Starting materials: 4-(4-bromo-1-butoxy)coumarin and salicylaldehyde. Fp.: 192–196° C.

Preparation of the title compound:
Starting material: methyl-3-aminocrotonate. Crystallized from ethanol. Fp.: 204–206° C.

EXAMPLE 30

4-[{2-(7-Coumarinyloxy)ethoxy}phenyl)-3,5-dimethoxycarbonyl-2,6-dimethyl-1,4-dihydropyridine.ethylacetate Preparation of the Intermediate 7-{2-(2-Formylphenoxy)ethoxy}coumarin.

Starting materials: 7-(2-bromo-ethoxy)coumarin and salicylaldehyde. Fp.: 131–134° C.

Preparation of the title compound:
Starting material: methyl-3-aminocrotonate. Crystallized from a mixture of methanol and ethylacetate. Fp.: 201–203° C.

IN VITRO EXPERIMENTS

The compounds were tested for antiviral activity by the Rega Institute (Leuven, Belgium).

The standard experiments for determining the biological activity of the compounds according to the invention were performed with CMV (Cytomegalovirus), varicella zoster virus, and RSV (respiratory syncytial virus). The details are shown in the Tables 1 to 3.

TABLE 1

CYTOMEGALOVIRUS

| | $IC_{50}$ (mg/ml) | | $CC_{50}$ |
|---|---|---|---|
| | AD-169 strain | Davis strain | (mg/ml) |
| Compound according to Example 24 | 2.4 | 2.3 | >200 |
| Reference compounds | | | |
| DHPG | 1.8 | 1.8 | >200 |
| (S)-HPMPC | 0.2 | 0.4 | 200 |

$IC_{50}$: concentration at which the virus production is inhibited by 50%.
$CC_{50}$ (mg/ml): concentration necessary to reduce cell growth by 50%.
DHPG = 9-[(1,3-dihydroxy-2-propoxy)methyl]guanine
(S)-HPMPC = (S)-1-(3-hydroxy-2-phosphonylmethoxypropyl)cytosine.

TABLE 2

VARICELLA ZOSTER VIRUS

| | $IC_{50}$ (mg/ml) | | | | |
|---|---|---|---|---|---|
| | TK + VZV | | TK − VZV | | |
| | OKA strain | YS strain | 07/1 strain | YS/R strain | $CC_{50}$ (mg/ml) |
| Compound according to Examples nrs | | | | | |
| 1 | 2.4 | 1.0 | 1.5 | 1.0 | 4.5 |
| 6 | 6.0 | 2.5 | 2.0 | 1.0 | 8.5 |
| 20 | 0.18 | 0.07 | 0.07 | 0.05 | 1.6 |
| 21 | 0.4 | 0.64 | 0.2 | 0.3 | 26 |
| 24 | ND | 2.5 | 2.5 | 1.5 | >200 |
| reference compounds | | | | | |
| ACV | 0.03 | 0.08 | 5 | 4 | >200 |
| BVDU | 0.001 | 0.001 | 20 | 40 | >200 |

$IC_{50}$: concentration at which the virus production is inhibited by 50%.
$CC_{50}$ (mg/ml): concentration necessary to reduce cell growth by 50%.
ACV = δ-(L-α-aminoadipyl-L-cysteinyl-D-valine
BVDU = carbocyclic bromovinyldeoxyuridine
ND: not determined.

TABLE 3

RESPIRATORY SYNCYTIAL VIRUS

| Compound according to Example nr. | $IC_{50}$ (mg/ml) | MTC (mg/ml) |
|---|---|---|
| 1 | 2.4 | 100 |
| 4 | 0.16 | 2.8 |
| 24 | 0.8 | 4.0 |
| 30 | 4.0 | 100 |

$IC_{50}$: concentration at which the virus production is inhibited by 50%.
MTC: Minimal toxic concentration. The concentration causing a microscopically detectable change in the normal cell morphology of HeLa-cells.
The above tables show that the compounds according to the invention are antivirally active substances.

What is claimed is:

1. A compound of formula I:

wherein:
R is CN, $NO_2$, or a —COOR' group, wherein R' is a lower alkyl group;
$R_1$ is $R_6$ or $R_4$;
$R_2$ is a lower alkoxy or $R_4$;
$R_3$ is H or $R_4$;
$R_4$ is a coumarin group of formula II:

$R_5$ is H, lower alkyl, lower alkoxy, halogene, nitro, hydroxyl or amino;
$R_6$ is H, lower alkyl, lower alkoxy, benzyloxy, cyano, nitro, carboxylic acid or carboxamide;
X is a single bond, —$(CH_2)_n$—O—, of —$(CH_2)_m$—Y—$(CH_2)_k$—O, wherein n is from 1 to about 6, m and k are each equal to or greater than 1 and the sum of m and k is equal to or less than 4;
Y is phenylene, cycloalkylene or a carbon atom substituted with 1 or 2 $C_1$–$C_2$-alkyl groups;
wherein lower alkyl, lower alkoxy, benzyloxy, phenylene and cycloalkylene may be substituted with 1–3 groups chosen from hydroxyl, cyano, amino, halogen and nitro;
wherein at least one of the groups $R_1$, $R_2$ and $R_3$ is $R_4$ or an N-oxide, stereoisomer or addition salt thereof with a pharmaceutically acceptable acid or base.

2. The compound of claim 1 wherein $R_6$ is a carboxylic acid esterified with a lower alkanol.

3. The compound of claim 1 wherein $R_6$ is a carboxamide substituted with 1–2 lower alkyl groups.

4. The compound of claim 1 wherein the halogen is a chlorine or fluorine.

5. The compound of claim 1 wherein at least one lower alkyl comprises a branched alkyl group having 1 to 6 carbon atoms.

6. The compound of claim 5 wherein the branched alkyl group has 1 or 2 carbon atoms.

7. The compound of claim 2 wherein the lower alkanol is a lower alkyl substituted with a hydroxyl group.

8. The compound of claim 1 wherein at least one lower alkoxy comprises a branched alkoxy group having 1 to 6 carbon atoms.

9. The compound of claim 8 wherein the branched alkoxy group has 1 or 2 carbon atoms.

10. The compound of claim 1 wherein the cycloalkyl comprises a cycloalkyl group having 3 to 8 carbon atoms.

11. The compound of claims 1, wherein if $R_1$, $R_2$, $R_5$ or $R_6$ comprise an alkyl group, the alkyl group comprises at least 2 carbon atoms.

12. The compound of claim 1, wherein if $R_1$, $R_2$, $R_5$ or $R_6$ comprise an alkoxy group, the alkoxy group comprises at least 2 carbon atoms.

13. A method for making an ester derivative of 1,4-dihydropyridine-5-carboxylic acid, the method comprising:

converting a coumarin derivative of formula III:

(III)

to an acetoacetate-ester of formula IV:

(IV)

wherein $R_5$ is a coumarin group of formula II:

(II)

reacting the acetoacetate-ester of formula IV with a benzylaldehyde of formula V:

(V)

and an R'-aminocrotonate; wherein $R_1$ is $R_6$ or $R_4$; $R_4$ is a coumarin group of formula II:

(II)

$R_6$ is H, lower alkyl, lower alkoxy, benzyloxy, cyano, nitro, carboxylic acid or carboxamide; and R' is a lower alkyl group.

14. A method for making an ester derivative of 1,4-dihydropyridine-5-carboxylic acid, the method comprising:

reacting $R_2$-4-chloroacetonacetate with benzylaldehyde of formula V:

(V)

wherein $R_1$ is $R_6$ or $R_4$; $R_2$ is a lower alkoxy or $R_4$; $R_4$ is a coumarin group of formula II:

(II)

and $R_6$ is H, lower alkyl, lower alkoxy, benzyloxy, cyano, nitro, carboxylic acid or carboxamide;

yielding a benzylidine of formula VI:

(VI)

wherein $R_1$ is $R_6$ or $R_4$; $R_2$ is a lower alkoxy or $R_4$; $R_4$ is a coumarin group of formula II:

(II)

and $R_6$ is H, lower alkyl, lower alkoxy, benzyloxy, cyano, nitro, carboxylic acid or carboxamide; reacting the resulting benzylidine of formula VI with an R'-3-aminocrotonate, wherein R' is a lower alkyl group;

yielding a 5-chloromethyl-1,4dihydropyridine derivative of formula VII:

(VII)

wherein $R_1$ is $R_6$ or $R_4$; $R_2$ is a lower alkoxy or $R_4$; $R_4$ is a coumarin group of formula II:

(II)

and R$_6$ is H, lower alkyl, lower alkoxy, benzyloxy, cyano, nitro, carboxylic acid or carboxamide);

reacting the 5-chloromethyl-1,4dihhydropyridine derivative of formula VII under basic conditions with a coumarin derivative of formula III:

(III)

wherein X is a single bond, —(CH$_2$)$_n$—O—, of —(CH$_2$)$_m$—Y—(CH$_2$)$_k$—O, wherein n is from 1 to about 6, m and k are each equal to or greater than 1 and the sum of m and k is equal to or less than 4; Y is phenylene, cycloalkylene or a carbon atom substituted with 1 or 2 C$_1$–C$_2$-alkyl groups; and R$_5$ is H, lower alkyl, lower alkoxy, hologene, nitro, hydroxyl, or amino.

15. A method for making an ester derivative of 1,4-dihydropyridine-5-carboxylic acid, the method comprising:
providing a coumarin derivative of formula VIII:

(VIII)

wherein R$_5$ is H, lower alkyl, lower alkoxy, hologene, nitro, hydroxyl, or amino; A is —(CH$_2$)n—, or —(CH$_2$)m—Y—(CH$_2$)$_k$, n is from 1 to about 6, m and k are each equal to or greater than 1 and the sum of m and k is equal to or less than 4; Z is a leaving group;

reacting the coumarin derivative of Formula VIII under basic conditions with a benzylaldehyde derivative of Formula V:

(V)

wherein R$_1$ is R$_6$ or R$_4$; and R$_6$ is H, lower alkyl, lower alkoxy, benzyloxy, cyano, nitro, carboxylic acid or carboxamide, yielding a Williamson ether of formula IX:

(IX)

reacting the Williamson ether of formula IX with an R'-aminocrotonate derivative, wherein R' is a lower alkyl group.

16. A pharmaceutical composition comprising the compound of claim 1 and a pharmaceutically acceptable carrier.

17. A method of treating a viral infection in a mammal, comprising administering a pharmaceutically effective amount of the compound of claim 1.

18. The method of claim 17 wherein the viral infection is adenovirus type 2, coxackie virus B4, cytomegalovirus, herpes simplex virus-2, HIV-1, HIV-2, influenza virus A, influenza virus B, parainfluenza-3 virus, polio virus-1, reovirus, respiratory syncytial virus, semliki forest virus, sindbis virus, vaccina virus, varicella zoster virus or vesicular stomatitus virus.

19. A method of treating high blood pressure in a mammal, comprising administering a pharmaceutically effective amount of the compound of claim 1.

20. A method of treating glaucoma in a mammal, comprising administering a pharmaceutically effective amount of the compound of claim 1.

* * * * *